United States Patent [19]

Frey et al.

[11] Patent Number: 4,728,730

[45] Date of Patent: Mar. 1, 1988

[54] SYNTHESIS OF NUCLEOSIDE THIOPHOSPHOANHYDRIDES

[75] Inventors: Perry A. Frey, Madison, Wis.; Hsu-Tso Ho, Lowell, Mass.

[73] Assignee: Wisconsin Alumini Research Foundation, Madison, Wis.

[21] Appl. No.: 650,299

[22] Filed: Sep. 12, 1984

[51] Int. Cl.$^4$ .......................................... C07H 19/067
[52] U.S. Cl. ........................................ 536/28; 536/29;
[58] Field of Search ............... 536/27, 28, 29; 514/51, 514/52

[56] References Cited

U.S. PATENT DOCUMENTS 3,846,402  11/1974  Eckstein et al. ...................... 536/27

OTHER PUBLICATIONS

Trowbridge et al., J. Amer. Chem. Soc., vol. 94, pp. 3816–3824, 1972.
F. Eckstein & R. Goody, 15 Biochemistry 1685–1691 (1976).
R. S. Goody & F. Eckstein, 93 J. Am. Chem. Soc. 6252–6257 (1971).
A. M. Michelson, 91 Biochem. Biophys. Acta 1–13 (1964).
J. Richard, H. Ho, & P. Frey, 100 J. Am. Chem. Soc. 7756–7757 (1978).
J. Richard & P. Frey, 104 J. Am. Chem. Soc. 3476–3481 (1982).
J. Richard & P. Frey, 105 J. Am. Chem. Soc. 6605–6609 (1983).
M. R. Webb, 19 Biochemistry, 4744–4748 (1980).
G. Lowe, et al., 22 Biochemistry 1229–1236 (1983).
G. Lowe & B. Sproat, J. Chem. Soc. Chem. Commun. 565–567 (1978).
E. F. Rossomando et al., 18 Biochemistry 5670–5674 (1979).
C. Lerman & M. Cohn, 255 J. Biol. Chem. 8756–8760 (1980).
P. Burgers & F. Eckstein, 255 J. Biol. Chem. 8229–8233 (1980).
E. Jaffe & M. Cohn, 254 J. Biol. Chem. 10839–10845 (1979).
E. Jaffe & M. Cohn 253 J. Biol. Chem. 4823–4825 (1978).
E. Jaffe & M. Cohn, 17 Biochemistry 652–657 (1978).
M. Cohn & A. Hu, 75 Proc. Nat. Acad. Sci. USA 200–203 (1978).

*Primary Examiner*—J. R. Brown
*Assistant Examiner*—L. Eric Crane
*Attorney, Agent, or Firm*—Quarles & Brady

[57] ABSTRACT

A method for preparing sulfur and/or selenium containing phosphoanhydrides that have at least a triphosphate moiety is disclosed, together with a cyclo-intermediate formed during the reaction. The method includes reacting a first compound having an available and reactive group selected from phosphorodihalidate, thiophosphorodihalidate, and selenic phosphorodihalidate (the compound having a remaining portion that does not interfere with the reaction), with a second compound having an available and reactive group selected from phosphate, thiophosphate, and selenic phosphate (the second compound also having a remaining segment that does not interfere with the reaction). The selection of the reactive groups is such that at least one of the reactive groups is the thio or selenic variant, and the selection of the remaining portion and segment are such that at least one is attached to a linking group selected from phosphate, thiophosphate, and selenic phosphate that links it to the available and reactive group. The reaction appears to be best suited for creating nucleoside thiotriphosphates.

6 Claims, No Drawings

SYNTHESIS OF NUCLEOSIDE THIOPHOSPHOANHYDRIDES

This invention was made with Government support under NIH Grant No. 5 RO1 GM 30480-03 awarded by the Department of Health and Human Services. The Government has certain rights in this invention.

BACKGROUND OF THE INVENTION

A. Field Of The Invention

This invention relates to an improved method for synthesizing sulfur and selenium containing phosphoanhydrides. It also relates to a unique family of cyclo-intermediates created during this synthesis. The invention is especially well suited for synthesizing nucleoside thiotriphosphates such as adenosine-5'-[2-thiotriphosphate].

B. Description Of The Art

Because of the important function that nucleotides and nucleosides have in the genetic make up of the body, they have been the subject of much study. Nucleotides can be defined as an organic compound having a nitrogenous base, a five carbon backbone (usually a sugar), and a phosphoric acid. Nucleosides are similar in structure, except that the phosphate group is not present.

Many nitrogenous bases are derived from purine and pyrimidine such as uracil, thymine, cytosine, 5-methyl cytosine, 5-hydroxy-methyl cytosine, adenine, guanine, 2-methyladenine, 1-methylguanine. Nucleosides are usually N-glycosides of these pyrimidine or purine bases. Among these are the ribonucleosides which contain D-ribose as the sugar component, and the 2' deoxyribonucleosides which contain 2'-deoxy-D-ribose as the sugar component. The most prevalent nucleosides are adenosine, guanosine, cytidine, uridine, 2' deoxyadenosine, 2' deoxyguanosine, 2' deoxycytidine, and 2' deoxythymidine.

The names for the corresponding nucleotides are the same except that "5'-phosphoric acid" is added. The nucleotides are also known by their abbreviations AMP, GMP, CMP, UMP, dAMP, dGMP, dCMP, and dTMP. These nucleotides also occur as the 5' di-phosphates and the 5' triphosphates (e.g. ADP, ATP).

A very important 5' tri-phosphate is adenosine 5' triphosphate ("ATP"). Its sulfur variant, adenosine-5' [2-thiotriphosphate] ("ATPBS") has been widely used in stereochemical studies of phosphotransferases and ATP-dependent synthetases. F. Eckstein and R. S. Goody, 15 Biochemistry 1685-1691 (1976); E. K. Jaffe and M. Cohn, 17 Biochemistry 652-657 (1978), 253 J. Biol. Chem. 4823-4825 (1978) and 254 J. Biol. Chem. 10839-10845 (1979). (The disclosures of these articles and of all other articles cited herein are incorporated by reference as if fully set forth herein.) Other variants of ATP (or other nucleoside tri-phosphates) where there has been substitution of one, two, three, or four sulfur or selenium for the phosphate-linked oxygen are also of interest. Also, it is of interest to create other types of triphosphate compounds that have selenic phosphate and thiophosphate groups, e.g. oligonucleotide thio-triphosphates.

A prior art synthesis of ATPBS was reported by R. S. Goody and F. Eckstein, 93 J. Am. Chem. Soc. 6252-6257 (1971), and Eckstein & Goody (1976) supra. They adapted a general procedure introduced by Michelson for synthesizing phosphoanhydrides, which is reported in A. M. Michelson, 91 Biochem. Biophys. Acta 1-13 (1964), to the preparation of sulfurcontaining nucleoside phosphoanhydrides. However, the overall yield of this process was low (12% for ATPBS). It can therefore be seen that it would be desirable to have a low cost procedure for making ATPBS and related sulfur and/or selenium containing triphosphate compounds in high yields.

SUMMARY OF THE INVENTION

The present invention generally relates to a method for preparing phosphoanhydrides that have at least a tri-phosphate moiety, and more specifically to a method of preparing ATPBS and related compounds. In one embodiment, one reacts a first compound having an available and reactive group selected from phosphorodihalidate, thiophosphorodihalidate, and selenic phosphorodihalidate, with a second compound having an available and reactive group selected from phosphate, thiophosphate, and selenic phosphate. The first and second compounds have remaining portions that do not interfere with the reaction. The selection of the reactive groups is such that at least one of the reactive groups is the thio or selenic variant. Also, the selection of the remaining portions is such that at least one is attached to a linking group selected from phosphate, thiophosphate, and selenic phosphate that links it to the available and reactive group for the compound.

The sulfur variants are the preferred embodiments (as opposed to the selenium variants) because sulfur is more closely related to the naturally occurring oxygen in physical properties. Moreover, the preferred process involves the use of nucleoside type moieties as the remaining portions of the compounds. In an especially preferred form, the sugar portion of a nucleoside is protected during at least a portion of the reaction by the use of a 2', 3' methoxymethylidene group.

This reaction can be schematically represented as follows:

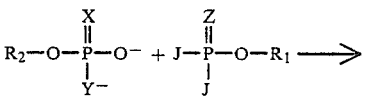

where J is halide, X, Y, and Z are selected from O, S and Se (and are the same or different but at least one is not oxygen), and $R_1$ and $R_2$ are the remaining portions. Preferably, Y is oxygen and at least one of X and Z is not oxygen. Further, at least one of $R_1$ and $R_2$ also comprises a linking group:

where W is selected from O, S, and Se. The linking group links the R portion to the reactive portion of the compounds.

Where $R_1$ and $R_2$ are nucleosides, it is best to use nitrogenous salts of the $R_2$ group, and to run the reaction in an aqueous-free organic solvent such as hexamethyl phosphoroamide. An aqueous work-up after the main reaction produces the final product. Typical reaction temperatures for nucleosides are 4° C. to 30° C.

Where it is desired to remove one of the R nucleoside groups, the other can be protected during the reaction by a group such as methoxy-methylidene. The group to be removed can then be cleaved by periodate, then the $IO^-_3$ and excess $IO^-_4$ can be reduced by a compound such as mercaptoethanol, then the protective group can be removed in acid (e.g. pH 2), and then the remainder of the periodate cleaved R group can be removed in base (e.g. pH 10). This yields a sulfur and/or selenium containing nucleoside triphosphate.

Another aspect of the invention is that a cyclic intermediate of the following formula is formed during the reaction prior to the aqueous work-up:

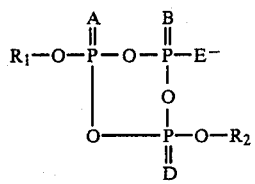

In this formula, $R_1$ and $R_2$ are organic moieties such as nucleosides, and A, B, D, and E are selected from O, S and Se (but not all four are oxygen). The primary utility of this intermediate is in preparing the final compounds of the above described process. However, certain of these compounds have value in and of themselves (such as for stereochemical studies). The addition of water opens the ring.

A theoretical aspect of the invention is the recognition that thiophosphate and selenic phosphate groups are generally very difficult to link with each other and/or phosphate groups. Thus, in accordance with the present invention, dihalidate variants are used to increase reactivity.

The objects of the invention therefore include:

a. Providing a method of the above kind in which certain sulfur and/or selenium containing phosphoanhydrides can be synthesized at lower cost.

b. Providing a method of the above kind for efficiently synthesizing nucleoside thio-triphosphates; and c. Providing an organic cyclo-intermediate of the above kind.

These and other objects and advantages of the invention will be apparent from the description which follows. In the description, reference is made to formula drawings. These are shown by way of illustration of the preferred embodiment of the invention, and this embodiment does not represent the full scope of the invention. Rather, the invention may be employed in other embodiments.

DESCRIPTION OF THE PREFERRED EMBODIMENT

A. The Materials Used

In the experiments below, barium oxide, calcium hydride, diphenylphosphorodichloridate, hexamethylphosphoroamide, 4 Å molecular sieves, phosphorus oxychloride, sodium periodate, thiophosphoryl trichloride, tri-n-butylamine, triethyl phosphate, triethyl orthoformate and tri-n-octylamine were purchased from Alrich Chemical. DEAE-Sephadex A-25 and adenosine were purchased from Sigma Chemical and Boehringer Mannheim, respectively; Dowex AG-50 ion exchange resin and deuterium oxide (88.7% $^2H$) were purchased from Bio-Rad Laboratories, and $H_2{}^{18}O$ was purchased from Monsanto Research Corporation, Mound Laboratory. AMPS and 2',3'-methoxymethylidene AMP were synthesized by published procedures. J. P. Richard and P. A. Frey, 104 J. Am. Chem. Soc. 3476–3481 (1982).

B. Purifications Of Solvents

For the experiments below, solvents were purified as follows. Triethyl-phosphate was mixed with barium oxide and allowed to stand for 24 hours before distilling in vacuo. Redistilled triethyl phosphate was stored over molecular sieves (4 Å) in the dark. Thiophosphoryl chloride and phosphorus oxychloride were redistilled and desiccated under $N_2$. Pyridine was mixed with calcuim hydride overnight, redistilled and stored over potassium hydroxide in the dark.

N,N-dimethylformamide was dried by mixing with powdered barium oxide and allowing the mixture to stand overnight. It was then distilled from alumina. Redistilled N,N-dimethylformamide was stored over molecular sieves (4 Å) in the dark. Tri-N-butylamine was stirred with calcium hydride for 12 hours and then distilled in vacuo. Redistilled tri-n-butylamine was described under $N_2$.

Triethylamine was redistilled before use. Hexamethylphosphoroamide was distilled in vacuo prior to being used. Ethyl ether, if not from a freshly opened can, was passed through an alumina (Basic X Type WB-5) column just prior to being used. Dioxane was stored overnight with molecular sieves (4 Å) and distilled. Redistilled dioxane stored over BaO in the dark was percolated through an alumina column prior to use. Small aliquots of alumina treated dioxane were tested for the presence of peroxides. They were mixed with equal volumes of water and a few crystals of KI were added. A yellow color from oxidation of $I^-$ to $I_2$ signaled the presence of peroxides. The alumina treatment was repeated until a colorless clear solution was obtained in the KI-test. Other solvents were obtained from commercial suppliers and used without further purification.

C. Description Of The Chromatography

In the experiments below, nucleotides synthesized were routinely purified by ion exchange column chromatography through DEAE-Sephadex A-25 using triethylammonium bicarbonate in the elution gradients. DEAE-Sephadex A-25 ion exccchanger was prepared by permitting the exchanger to swell in 1.0M triethylammonium bicarbonate for several hours. After being packed in a column having the desired dimensions, the column of ion exchanger was washed first with four volumes of 1.0M $KHCO_3$ and then with four volumes of 0.1M triethylammonium bicarbonate buffer at pH 7.6. Regenertion of the column was by a similar procedure.

Triethylammonium bicarbonate was prepared by bubbling $CO_2$ gas generated from dry ice through a glass filter and into a 1.0M aqueous solution of triethylamine with stirring until the pH of the solution reached 7.6. The stock solution was stored at room temperature in a tightly capped bottle.

Nucleotides in solution at pH 7.6 with ionic strength at 0.1M or less were absorbed to columns of DEAE-Sephadex A-25 that had been equilibrated with 0.1M triethylammonium bicarbonate at pH 7.6 (see above). Nucleotides and thionucleotides were eluted from the columns using linear gradients of triethylammonium bicarbonate at pH 7.8. The gradients were prepared by adding equal volumes of two different concentrations of triethylammonium bicarbonate buffer to two identical flasks connected by a bridge filled with the buffer of lower concentration. The latter buffer was stirred continuously while the gradient was drawn from this flask to feed the column. Fractions were collected, and those containing nucleotides were identified by $A_{260}$ measurements. Peak fractions were pooled and the buffer salts removed by flash evaporation using a rotary evaporator connected to a vacuum pump. The bath temp was kept below 30° at all times. The initial residue was twice taken up in 95% ethanol and again evaporated to insure that all the buffer salts were removed. The final residue was dissolved in a minimum amount of water and stored at $-15°$ C. after the pH had been adjusted to 10 by addition of triethylamine.

In preparation for further use in synthesis, the triethylammonium salts of nucleoside phosphorothioates were converted to tri-n-octylammonium salts to render them soluble in organic solvents. The triethylammonium salt of a nucleotide was passed through a column of Dowex-50 (pyridinium form) which had at least a 20-fold excess of exchange capacity. The flow-through contained the pyridinium salt of the nucleotide, which was evaporated to dryness by rotary evaporation in vacuo. The residue was dissolved in a minimum volume of methanol; and tri-n-octylamine was added to the solution (one equivalent for all nucleoside monophosphates or monophosphorothioates, two equivalents for nucleoside diphosphates or thiodiphosphates). After stirring the mixture until it became clear, methanol was removed in vacuo. The residue was desiccated with $P_2O_5$, under vacuum for 20 hrs at 25° to remove traces of methanol and water. Analogous procedures would be used for other nucleoside type moieties.

D. $^{31}P$-NMR Analysis

For the experiments below, proton spin decoupled $^{31}P$-NMR spectra of nucleotides were obtained on 2 to 2.5 mL samples consisting of 1 to 5 mM nucleotide dissolved in 40% $D_2O$ at pH 9-10 and containing 50 mM EDTA. The spectrometer was field frequency locked to the deuterium resonance of the solvent. Spectra were obtained using a Bruker 200 mHz, a Bruker 360 mHZ and a Nicolet 200 mHz spectrometer. All chemical shifts were related to that of 1 N (0.33M) $H_3PO_4$, dissolved in $D_2O$ as an external reference.

E. Formula For Synthesis of ADPBS

Adenosine -5'-[2-thiodiphosphate] ("ADPBS") is a precursor to one of the "second compounds" referred to in claim 1 of this patent application. While there is a known means of synthesizing it, the preferred synthesis is schematically depicted below (extra hydrogens on carbon are not always depicted):

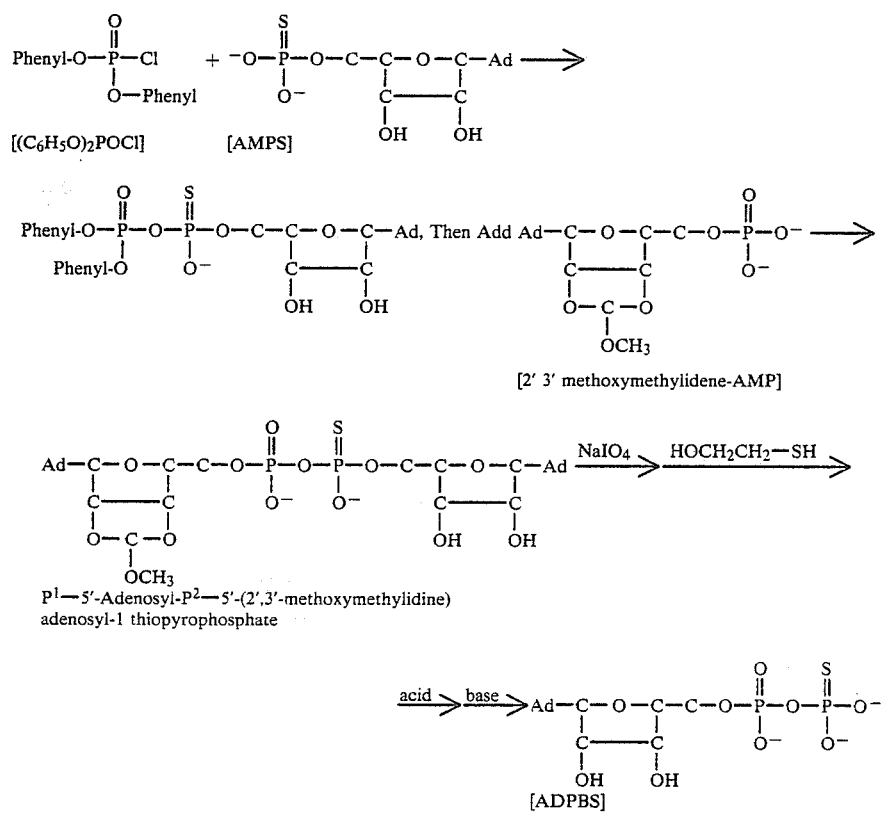

F. Specifics Of The Synthesis Of ADPBS

An aqueous solution containing 1 mmol of the triethylammonium salt of 2', 3'-methoxymethylidene-AMP was dried by flash evaporation in a rotary evaporator. After dissolving the residue with 20 mL of methanol, 1 mmol of tri-n-octylamine (0.45 mL) was added to the solution. The mixture was stirred until it became clear. After removing methanol by rotary evaporation, the residue was further dried by twice dissolving it in anhydrous N,N-dimethylformamide and removing the solvent by rotary evaporation.

The dried 2', 3'-methoxymethylidene-AMP was desiccated in vacuo over $P_2O_5$ for 24 hrs in preparation for coupling to $P^1$-bis (phenyl) $P^2$-5'-adenosyl 2-thiopyrophosphate prepared as follows: The triethylammonium salt of AMPS (2 mmol) was dried by rotary evaporation to remove water. Methanol (40 mL) and tri-n-octylamine (2 mmol, 0.9 mL) were added to the nucleotide. The mixture was stirred until a clear solution was obtained and then dried by rotary evaporation. The residue was further dried by twice dissolving it in anhydrous N,N-dimethylformamide and removing the solvent by rotary evaporation. The AMPS was then dried in vacuo over $P_2O_5$ for 24 hrs.

The mono tri-n-octylammonium salt of AMPS was dissolved in 8 mL of triethylphosphate, and to the solution were added diphenyl phosphorochloridate (3 mmol, 0.64 mL) and tri-n-butylamine (4 mmol, 1 mL). The flask was stoppered and the mixture stirred at ambient temperature for 3 hrs. A mixture consisting of 150 mL of petroleum ether (b. p. 60°–80° C.) and 50 mL of diethyl ether (new can) was added to the solution with stirring at the end of the 3 hr period. This mixture was kept at 0° C. for 30 min. The ether layer was decanted and 4 mL of dioxane was added to the residue. The solution was evaporated to dryness using a rotary evaporator. The dried mono tri-n-octylammonium salt of 2',3'-methoxymethylidene-AMP was dissolved in 2 mL of pyridine, transferred to the flask containing activated AMPs, and the reaction mixture was stirred at ambient temp for 16 hrs. After removing pyridine by rotary evaporation, diethyl ether (20 mL) was added to the residue and water used to extract nucleotides until the $A_{260}$ of aqueous extracts were less than 0.5. The pH of the combined aqueous extract was immediately adjusted to 8 by addition of NaOH to avoid losing the methoxymethylidene group.

To cleave off one nucleotide, three mmol of $NaIO_4$ were added and the solution kept at ambient temp for 30 min, at which time 30.0 mmol of 2-mercaptoethanol were added to quench the periodate degradation and reduce $IO_4$ and $IO_3$ to $I^-$. To remove the methoxymethylidene, the pH of the solution was adjusted to 2 by adding HCl. After 100 min at 25° C., the pH was adjusted to 10.5 by addition of NaOH. The base was added in order to remove the periodate cleaved residue. This solution was heated at 50° C. for 30 min.

The solution was diluted to 2 liters and divided into two 1-liter aliquots, each of which was passed through a 4×50 cm column of DEAE-Sephadex A-25 in the $HCO_3$ form. Nucleotides were eluted from each column using a triethylammonium bicarbonate gradient having a total volume of 7 liters (3.5 liters of each component) and increasing from 0.2 to 0.45M. Fractions 23 mL in volume were collected at 16 min intervals, and selected fractions were analyzed for $A_{260}$ and reactivity with 5,5'-dithiobis-(2-nitrobenzoate). ADPBS appeared as a prominent band in fractions 240-280. Pooled fractions were desalted as described above, yielding ADPBS in an overall yield of 58%.

The $^{31}$P-NMR spectrum (proton spin decoupled) of ADPBS exhibited a P (alpha) doublet at $-11.79$ ppm and a P (beta) doublet at 32.82 ppm with J alpha, beta$=31.74$ Hz, in agreement with the values reported for [Beta-$^{18}$O] ADPBS. E. K. Jaffe and M. Cohn, 17 Biochemistry 652–657 (1978). Thin layer chromatography also showed that the ADPBS prepared in this manner comigrates with authentic [Beta-$^{18}$O] ADPBS prepared by the procedure of J. P. Richard and P. A. Frey, 104 J. Am. Chem. Soc. 3476–3481 (1982).

G. Formula For Synthesis Of 2', 3'-Methoxymethylidene-ADPBS

A schematic of the synthesis of one of the "second compounds" referred to in claim 1 of this application is as follows (extra hydrogens on carbon are not always depicted):

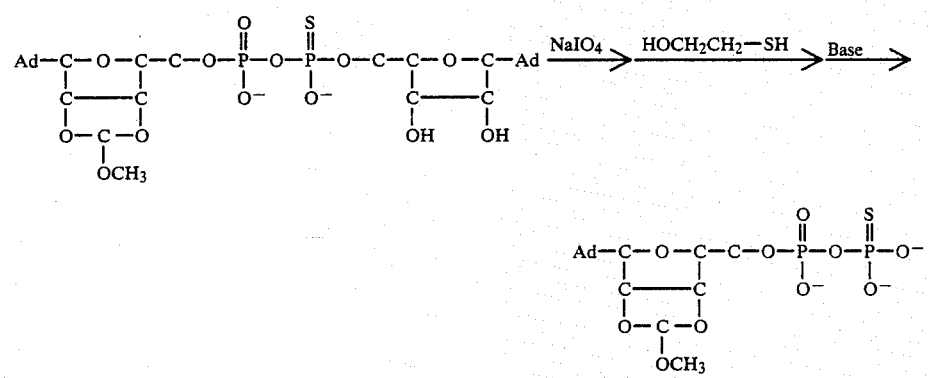

[2'3'-methoxymethylidene-ADPBS]

H. Synthesis Of The 2', 3'-Methoxymethylidene-ADPBS $P^1$-5'-adenosyl-$P^2$-5'-(2',3'-methoxymethylidene)adenosyl-1-thiopyrophosphate was synthesized as described above in parts E and F. See also J. P. Richard and P. A. Frey, 104 J. Am. Chem. Soc. 3476–3481 (1982) for a similar synthesis (except that the $R_P$ and $S_P$ epimers were not separated). The mixture was converted to 2',3'-methoxymethylidene ADPBS (rather than all the way to ADPBS) by the following procedure:

$P^1$-5'-adenosyl-$P^2$-5'-(2',3'-methoxymethylidene)adenosyl-1-thiopyrophosphate (300 Mumol) was dissolved in 30 mL of water and the pH adjusted to 8.0. $NaIO_4$ (450 Mumol) was added to the solution. After stirring at ambient temp for 30 min, 5 mmol of 2-mercaptoethanol was added and the pH was adjusted to 10.5 with NaOH. The reaction mixture was maintained at 50° C. for 30 minutes and then diluted with water to a final volume of 200 mL in preparation for DEAE-Sephadex A-25 column chromatography through a 2.5×40 cm column of DEAE-Sephadex A-25.

A 3.5 liter linear gradient of triethylammonium bicarbonate increasing from 0.1M to 0.5M was used to elute the compounds. Fractions of 23 mL were collected at a rate of 1.5 mL/min. The product appeared as an isolated band of 5,5-dithio-bis(2-nitrobenzoate)-sensitive and $A_{260}$-absorbing material in fractions 119 to 142, which were pooled and desalted. The pooled fractions contained 223.3 Mumol of 2',3'-methoxymethylidene-ADPBS, an overall yield of 74.4% based on the extinction coefficient of 24,000 $M^{-1} cm^{-1}$ for $P^1$-adenosine-$P^2$-2',3'-methoxymethylidene-adenosine-5'-(1-thiodiphosphate) and 15,000 $M^{-1} cm^{-1}$ for 2',3'-methoxymethylidene-ADPBS.

The 2',3'-methoxymethylidene-ADPBS obtained gave a positive reaction with 5,5-dithio-bis-(2-nitrobenzoate), an identical UV absorption spectrum as that of 2',3'-methoxymethylidene-AMP and was not degraded by $NaIO_4$. The $^{31}P$-NMR spectrum of 2',3'-methoxymethylidene-ADPBS gave two doublets with chemical shifts and a coupling constant essentially identical to that of ADPBS: P (alpha) $-11.07$ ppm, and P (beta) 33.05 ppm, with J alpha, beta=31.70 Hz.

I. Synthesis Of The Cyclo-Intermediate

An example of one of the "first compounds" referred to in claim 1 of this patent is adenosine-5'-phosphorodichloridate. To obtain this compound one reacts adenosine with $POCl_3$ (extra hydrogens on carbon are not always depicted below):

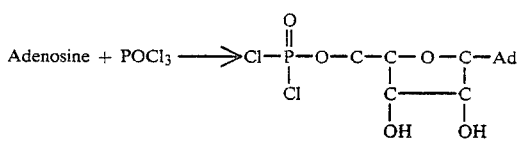

This "first compound" has an available and reactive phosphorodichloridate group, and a remaining portion that does not interfere with the remainder of the reaction.

The crude adenosine-5'-phosphorodichloridate is then reacted with the previously synthesized 2',3'-methoxymethylidene-ADPBS (the "second compound"). The available and reactive group on the second compound is

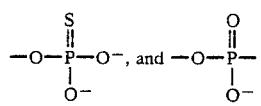

is a phosphate "linking group" to the remaining organic segment.

The resulting cyclo-intermediate is:

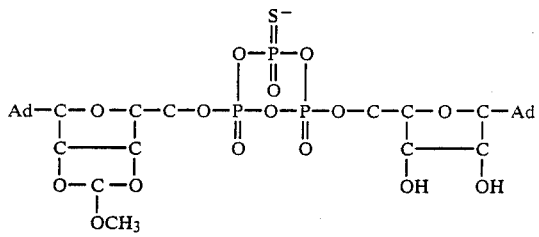

It should be noted that in solution the sulfur may at times be double bonded to the oxygen and the non-bridging oxygen on that phosphorus may instead carry the charge.

Upon aqueous workup, the ring opens to form the following triphosphate:

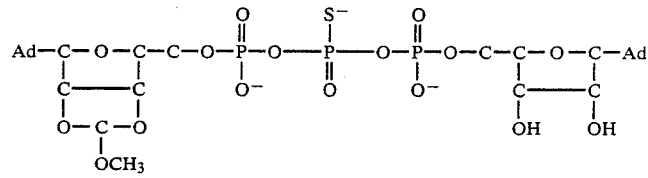

In greater detail, this synthesis is as follows: Adenosine (250 Mumol), which had been desiccated over $P_2O_5$, in vacuo at 110° C. overnight, was dissolved in 0.7 mL of triethyl phosphate by cautiously swirling the suspension in a distillation flask over an open flame. The clear solution was immediately cooled in an ice-water bath and $POCl_3$ (325 Mumol) added. The reaction mixture was stirred magnetically at room temp for 30 min. Triethyl phosphate, unreacted phosphorus oxychloride and HCl generated in the reaction were removed by vacuum distillation at 35°–40° into a receiving flask cooled in an ice-water bath.

Separately, the triethylammonium salt of 2'3'-methoxymethylidene-ADPBS (100 Mumol) in aqueous solution was concentrated by rotary evaporation and the resulting residue dissolved in 2 mL of methanol. Two equivalents (200 Mumol) of tri-N-butylamine was added and methanol removed by rotary evaporation in vacuo. The residue was dissolved in 2 mL of water, frozen as a thin film on the wall of the flask and lyophilized to dryness (12 hrs).

The lyophilized tri-N-butylammonium salt of 2',3'-methoxymethylidene-ADPBS was dissolved in 1.0 mL of hexamethylphosphoroamide and transferred to the flask containing the crude adenosine-5'-phosphorodichloridate, together with a 0.5 mL hexamethylphosphoroamide wash. The reaction flask was sealed and the solution stirred at room temp for 24 hrs. Diethyl ether (20 mL) was added and the resulting suspension centrifuged.

After decanting the supernatant fluid, the precipitate was dissolved with 10 mL of 1M triethylammonium bicarbonate and stirred at ambient temp for 1 hr. The solution was diluted to 150 mL and applied to a 2.5×40 cm column of DEAE-Sephadex A-25 in the $HCO_3$ form. The column was eluted with a linear gradient of triethylammonium bicarbonate increasing in concentration from 0.15M to 0.5M and formed from 1.2 L of each component. The flow rate was 1 mL $min^{-1}$ and 12 mL fractions were collected. The desired products appeared in fractions 149 to 179 as a prominent band detected by $A_{260}$ measurements. Fractions 50-80 contained a less prominent band of AMP.

Fractions 149-179 were pooled and desalted as described above. The yield of $P^1$-5'-adenosyl-$P^3$-5'-(2',3'-methoxymethylidene)-adenosyl-2-thiotriphosphate ranged between 60 and 65%. The major product was judged to be the above named compound on the basis of its $^{31}$P-NMR spectrum. The proton spin decoupled $^{31}$P-NMR spectrum consisted of two triplets—one centered at $=-11.71$ ppm assigned to $P^1$ and $P^3$, and a second at $=30.65$ ppm assigned to $P^2$—in a 2:1 integration ratio with a coupling constant of 24.91 Hz.

J. Conversion Of $P^1$-5'-Adenosyl-$P^3$-5'-(2',3'-Methoxymethylidene) Adenosyl-2-Thiotriphosphate To ATPBS The triethylammonium salt of $P^1$-5'-adenosyl-$P^3$-5'-(2',3'-methoxymethylidene) adenosyl-2-thiotriphosphate (240 $A_{260}$ units) in 2 mL of aqueous solution was adjusted to pH 8.4. Sodium metaperiodate (15 Mumol) was added with stirring to cleave a nucleoside. After reaction at ambient temp for 20 min, 150 Mumol of 2-mercaptoethanol were added. The pH was then adjusted to 2.0 by addition of 1 N HCl to cleave the methoxymethylidene. The solution was maintained at ambient temp for 120 min and then readjusted to pH 10.5 by addition of 1 N NaOH.

The solution was then heated to and maintained at 50° C. in a water bath for 20 min. It was diluted with water to 20 mL and subjected to ion exchange chromatography through a 1.5×15 cm column of DEAE-Sephadex A-25 in the $HCO_3$ form. The column was eluted with a linear gradient of triethylammonium bicarbonate increasing in concentration from 0.2M to 0.6M and formed from 350 mL of each component. Fractions 4.5 mL in volume were collected at 10 min intervals. A single prominent band of $A_{260}$ positive material appeared in fractions 28-36, which were pooled and desalted. The product was identified as the expected $R_p$- and $S_p$-epimer mixture of ATPBS by its $^{31}$P-NMR spectrum and as a substrate for yeast hexokinase, which accepted the $S_p$ epimer as a substrate. The yield of ATPBS by this process was 86%.

K. Variations

It will be appreciated by those skilled in the art that while a synthesis of ATPBS has been shown above, many additional modifications and changes may be made to the preferred embodiment without departing from the spirit and scope of the invention. The invention should, therefore, not be limited to the specific description of the preferred embodiment.

For example, while a triphosphate moiety in ATPBS is produced, a triphosphate moiety might also appear as part of a group of four or more phosphates linked together. Also, while a phosphorodichloridate is used, one or more other halides (e.g., bromine, iodine, and/or fluorine) could be substituted for one or both chlorines.

Further, while the example above shows only one of the phosphates being a thiophosphate, two or more could be thiophosphates (e.g., replace $POCl_3$ with $PSCl_3$). Also, the stereochemistry in the drawings is not the only stereochemistry that is possible. Moreover, appropriate selenic triphosphates could be made such as:

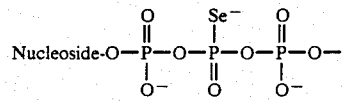

Also, while nucleoside variants are of primary interest, other biological compounds having triphosphate type groups could be synthesized in an analogous fashion, such as polynucleotide tri-phosphates.

It should also be noted that the claims are meant to include all forms of salts of these compounds, the compounds in solution, and compounds where the negative charge has migrated to the double bonded oxygen, sulfur or selenium. Further, the term "nucleoside" is to be given the broad meaning of this specification (which includes variants such as the deoxy-nucleosides, and protected variants, methylated groups and the like).

We claim:

1. A cyclic compound having the following formula:

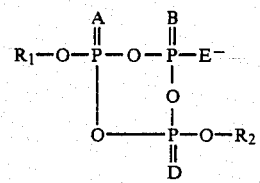

where $R_1$ and $R_2$ are nucleoside moieties, where A, B, D and E are selected from oxygen and sulfur, and where one of A, B, D and E is not oxygen.

2. A process for preparing a nucleoside thiophosphoanhydride having a thiotriphosphate moiety, comprising the steps of:
reacting in a liquid solvent a first compound having a first moiety selected from phosphorodihalidate and thiophosphorodihalidate
with a second compound having a second moiety selected from phosphate and thiophosphate
said reaction creating a cyclic intermediate;
the reaction prior to the formation of the cyclic intermediate being run at conditions suitable to keep the solvent in its liquid form;
the selection of said first and second moieties being such that one of them is the thio variant;
the selection of the first and second moieties being such that prior to the formation of the cyclic intermediate one is attached to a linking group selected from phosphate and thiophosphate that links it to a nucleoside moiety; and
adding water to the cyclic intermediate whereby the nucleoside thiophosphoanhydride is formed.

3. A process for preparing a nucleoside thiophosphoan hydride having a thiotriphosphate moiety, comprising the steps of:
reacting a first compound having a first moiety selected from phosphorodihalidate and thiophosphorodihalidate
with a second compound having a second moiety selected from phosphate and thiophosphate
said reaction creating a cyclic intermediate;
the reaction prior to the formation of the cyclic intermediate being run at a temperature between 4° C. and 30° C. in an essentially aqueous free polar organic liquid solvent such that the cyclic intermediate is formed;

the selection of said first and second moieties being such that one of them is the thio variant;

the selection of the first and second moieties being such that prior to said formation of the cyclic intermediate one is attached to a linking group selected from phosphate and thiophosphate that links it to a nucleoside moiety; and adding water to the cyclic intermediate to form the nucleoside thiophosphoanhydride.

4. The process of claim 3, wherein the cyclic intermediate has two nucleoside moieties.

5. The process of claim 3, wherein the nucleoside moiety is protected during at least a portion of the reaction by a 2′, 3′-methoxymethylidene group.

6. The process of claim 3, wherein the nucleoside moiety is a purine nucleoside.

* * * * *